United States Statutory Invention Registration [19]

[11] Reg. Number: H633

McLellan [43] Published: Jun. 6, 1989

[54] METHOD OF PREDICTING DUCTILITY OF A METALLIC CAST EUTECTIC ALLOY AND EQUATION THEREFOR

[75] Inventor: Dale L. McLellan, Bellevue, Wash.

[73] Assignee: The United States of America as represented by the Secretary of the Air Force, Washington, D.C.

[21] Appl. No.: 536,753

[22] Filed: Sep. 28, 1983

[51] Int. Cl.[4] ..... G01N 17/00
[52] U.S. Cl. ..... 73/87
[58] Field of Search ..... 73/87

*Primary Examiner*—John F. Terapane
*Assistant Examiner*—Eric Jorgensen
*Attorney, Agent, or Firm*—Bobby D. Scearce; Donald J. Singer

[57] ABSTRACT

The invention is a method of predicting ductility of a metallic cast eutectic alloy; the discovery of a microstructural function based upon manufacturing steps that influence ductility; and including the microstructural characteristics of the number of cells of a primary metal of the alloy such as aluminum in an aluminum silicon magnesium alloy, the silicon eutectic, and the lack of soundness, i.e., porosity; and the discovery of a ductility prediction equation.

2 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

TENSILE SPECIMEN
CHILLS
INSULATED INGATES AND RISERS
INSULATED BLIND RISERS

METHOD OF PREDICTING DUCTILITY OF A METALLIC CAST EUTECTIC ALLOY AND EQUATION THEREFOR

The government has rights in this invention pursuant to contracts No. F33615-80-C-3209 awarded by the U.S. Air Force.

TECHNICAL FIELD

The invention relates to a method of predicting ductility of a metallic cast eutectic alloy and the discovery of an equation therefor.

BACKGROUND ART

Castings made of alloys in which aluminum is the primary metal, for example, present serious quality control problems because the castings produced within a production run vary substantially in physical properties. Tensile properties may vary between casting zones in the same casting due to, for example, differences in local rates of solidification. Natural variations may also occur between castings due to slight changes within the acceptable limits for adding of the constituents to form the alloy and the latitudes of time and temperature of heat treatment and processing.

Present practice in the casting art, for example, aluminum alloys, is not capable of economically mass producing castings of statistically controllable or predictable properties. Furthermore, the tests of which one skilled in the art can usually select for determining mechanical properties such as percent elongation or ductility, yield strength, or tensile strength, tend to weaken or destroy the casting.

In more recent prior art, mechanical properties of castings have been ascertained by nondestructive procedures wherein test bars poured from the same metal and at the same time as the actual casting were destructively tested and by means of coupon test bars which are poured as an integral part of the casting and broken off at the time of completion of any heat treatment of the casting. In the latter procedure the coupon test bars are also destructively tested. However, both the former and the latter procedure, exemplified by U.S. Pat. No. 3,496,766, provide a mere differential determination of the structural properties of the casting. Both methods are therefore incapable of providing reliable information of the properties of the alloy in a particular zone which may have responded to heat treatment differently from another zone.

U.S. Pat. No. 4,381,666, of which the present inventor was a coinventor, provided a method based on the discovery of a unique relationship which correlates a microstructural parameter of a cellular alloy sample to ductility. The method includes counting substantially all of the metal cells of the primary metal within a surface area of a selected zone and correlating the number of metal cells per unit area to the ductility of the zone. The number of cells is correlated to the ductility of the cellular alloy by means of the equation:

$$EL = e^{\left(\frac{ANB-C}{D}\right)}$$

where

EL = total average elongation (ductility) in percent,

N = number of cells of the primary metal of the alloy counted per unit area,

A, B, C, D = empirical constants.

Other known prior art include the following

U.S. Pat. No. 3,086,391, Schmitt-Thomas et al

U.S. Pat. No. 3,586,546, Averbach et al

U.S. Pat. No. 3,940,976, Fastner

U.S. Pat. No. 4,063,644, Hoffman et al

Other publications

Use of Covariograms For Dendrite Arm Spacing, by R. Alberny, J. Serra, and M. Turpin;

Dendrite Cell Size, by R. E. Spear, Rsch. Engr. and G. R. Gardner, Asst. Chief, Castings and Forgings Div., Alcoa Research Laboratories, Cleveland;

Quality Control Practices, by Emmett N. Bossing and John J. Hall The Relation of Ductility To Dendrite Cell Size In A Cast, Al-Si-Mg Alloy, by S. F. Frederick and W. A. Bailey;

LEITZ-T.A.S. Texture Analysing System, Ernst Leitz GmbH Wetzlar and Robert Bosch Fernsehanlagen GmbH, Darmstadt.

DISCLOSURE OF THE INVENTION

The invention is a method of predicting ductility of a metallic cast eutectic alloy, a ductility prediction equation, and a microstructural function which accounts for the manufacturing steps that influence ductility, the latter being used in the equation.

The method includes counting substantially all of the cells of a primary metal of a metallic cast eutectic alloy within a surface area unit of the alloy. Then, the aspect ratio of eutectic particles and the porosity of the alloy are determined by well-known methods which include measuring with a calibrated-lens microscope or measuring with a computer aided microscope. With this information the ductility of the unit area is predicted by relating the cells per unit with the aspect ratio of the eutectic particles and the porosity. Relating the cells per unit with the aspect ratio of the eutectic particles and the porosity is accomplished with the equation according to the invention. Development and use of aspect ratio are new concepts, as is the use of porosity.

Further advantages of the invention may be brought out in the following part of the specification wherein small details have been described for the competence of the disclosure, without intending to limit the scope of the invention which is set forth in the appended claims.

BRIEF DESCRIPTION OF THE DRAWINGS

Referring to the accompanying drawings which are for illustrative purposes.

BEST MODE FOR CARRYING OUT THE INVENTION

Figure 1:
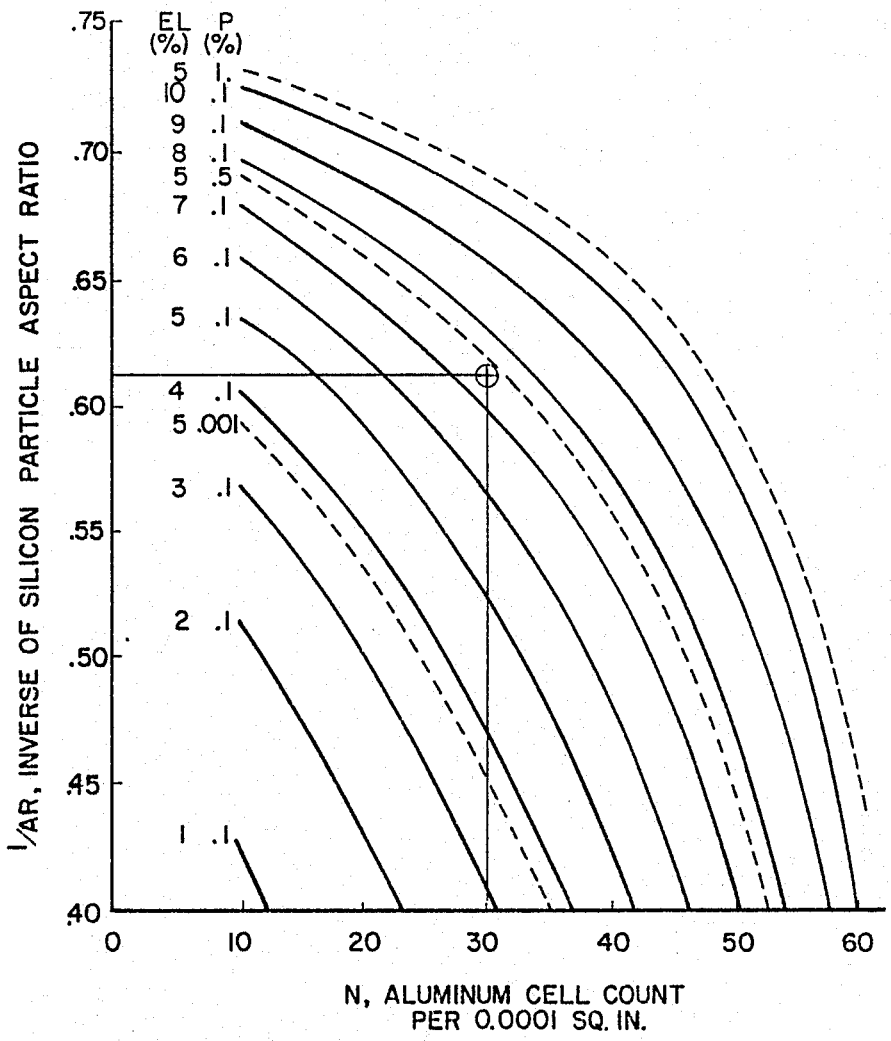
FIG. 1 is a graph in which the inverse of the silicon (eutectic) particle aspect ratio is plotted against the aluminum cell count per 0.0001 square inch, and the graphs are drawn in relation thereto from calculations made according to the invention.
Figure 2:
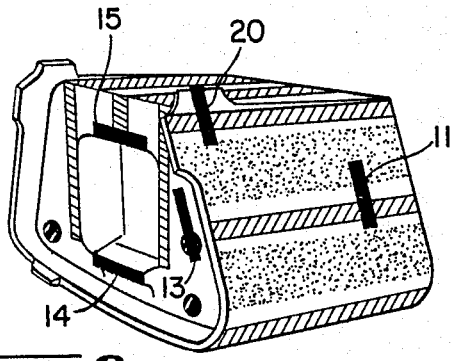
FIGS. 2–5 are various views of an air launched cruise missle tank casting made of A357 - T6 aluminum alloy and illustrate the location of tensile specimens for which ductility was predicted and measured, and also illustrating the location of chills, insulated ingates and risers, and insulated blind risers.
Figure 3:
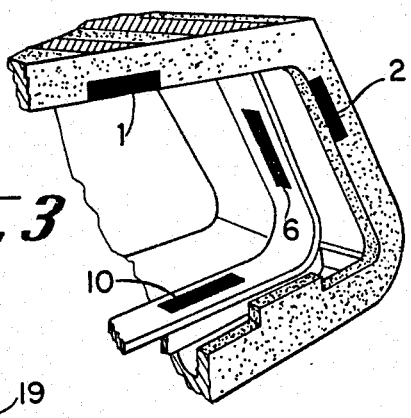
Figure 4:
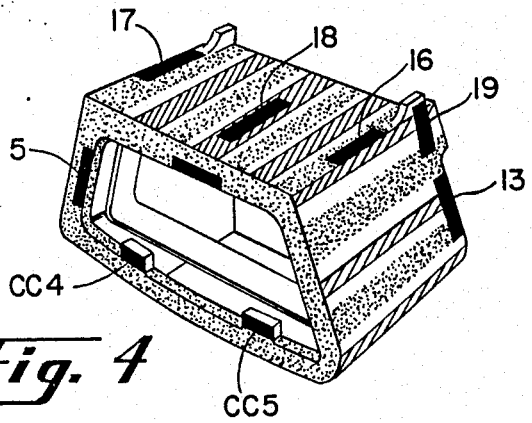
Figure 5:
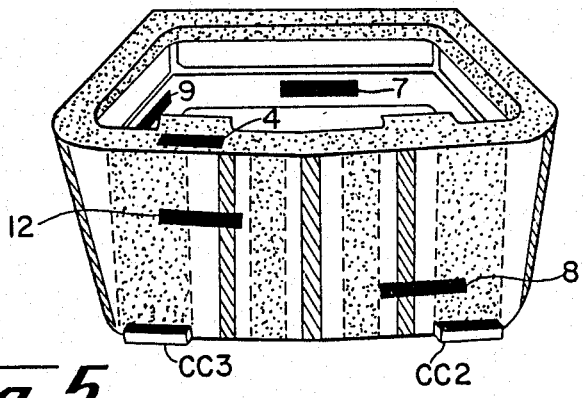

The ductility prediction equation has been established to predict ductility of aluminum silicon magnesium alloy castings, for example, in the fully heated T6 condition. This equation and method are considered usable for any metallic cast eutectic alloy. The basis of the equation is the microstructural characteristics of the aluminum cells, aluminum being the primary metal of the alloy, the silicon eutectic, and the lack of soundness, that is, the porosity of the alloy.

As indicated above and in U.S. Pat. No. 4,381,666, the expression:

$$EL = e^{\left(\frac{1.5\,N^{0.543}-4.81}{2.86}\right)}$$

was developed:, EL being the ductility in percent, N being the number of aluminum cells counted in an area of 0.0001 square inch, and the constants A, B, C, and D, respectively, 1.5, 0.543, 4.81, and 2.86 are constants that apply to the A357-T6 aluminum alloy.

Refinement of the above initial expression accounts for silicon particle eutectic modification from alloying, interactions with solidification rate, and solution heat treatment. All of these effects are conducive to ductility.

According to the invention, the above initial analytical expression has been modified for both user convenience and to create compatibility with related criteria established by Drouzy, et. al., of the Centre Technique des Industries de La Fonderie (CTIF) of Paris, France. By destruction of an aluminum alloy, Al-Si 7 Mg 06, about the same as A357, they postulated a quality index equation as follows:

$$Q = TUS + k\ \mathrm{Log}_{10}\ EL$$

where

Q=the quality of an aluminum alloy casting, depending upon the fineness of the primary metal (aluminum) cells, how well the eutectic is modified, and the soundness of the structure;

TUS=is the tensile ultimate strength; and k=is an age hardening coefficient.

They also proposed a yield strength equation, namely:

$$YS = TUS - b\ \mathrm{Log}_{10} EL - c,$$

where b and c are constants, like k for the alloy. They determined that Q was not totally independent of YS. However, according to the invention, it is desirable to have modified quality only dependent on EL.

Then, further according to the invention, by subtracting YS from Q gives a modified quality index, $Q_A$. Thus, $$Q_A = (Q - YS)$$

$$Q_A = (k+b)\mathrm{Log}_{10} EL + c.$$

According to the invention, the above expression was then rearranged to predict ductility.

$$EL = 10[(Q_A - c)/(k+b)]$$

It was determined that to estimate ductility from microstructure, $Q_A$ had to be replaced by a microstructural function M. The function M was developed to account for manufacturing processes that influence ductility. Experimental data was obtained to establish the necessary criteria, as follows:

$$M = C1(N_{0.5}) - C_2(N^{0.5}/AR) + C_3(1/AR) - C\text{-}(P^{0.5}) - C_5,$$

where $C_1(N^{0.5})$=or represents solidification rate (SR); SR is determined by counting the aluminum cells; a greater rate is indicated by more cells, and vice versa. The cells can be counted with a computer aided microscope. First, a cross section of the alloy is studied to identify the aluminum cells, and the cells are then counted in the field of examination. The SR can also be determined with thermocouples.

$C_2(N^{0.5}/AR)$=or represents SR and eutectic modification (EM) interaction; AR is aspect ratio, that is, geometric shape as defined by the average ratio of maximum to minimum particle dimensions of the eutectic (silicon) particles;

$C_3(1/AR)$=or represents EM from alloying and solution heat treatment;

$C_4(P^{0.5})$=or represents porosity, percentage coverage, ductility reduction; and $C_5$=or represents chemistry of alloy system.

For an A357 aluminum alloy, with M in units of ksi, coefficients from statistical multiple regression are $C_1=14.72$, $C_2=18.71$, $C_3=159.7$, $C_4=14.3$, and $C_5=82.8$.

Then, substituting M for the modified quality index allows ductility estimates:

$$EL = 10[(M-c)/(k+b)],$$

or substituting for M $$EL = 10\ [\{C_1(N^{0.5}) - C_2(N^{0.5}/AR + C_3(1/AR) - C_4(P^{0.5}) - C_5 - c\beta),/(k+b)],$$

Then, using CTIF values of b=8.71 ksi, c=1.89 ksi, and k 21.77 ksi, the working form of the inventive equation for an A357 aluminum alloy is:

$$EL = 10[0.48(N^{0.5}) - 0.61(N^{0.5}/AR) + 5.24(\text{-}1/AR) - 0.47(P^{0.5}) - 2.78].$$

This expression can be used analytically as stated above or to develop a series of graphs for which an example is shown in FIG. 1. In the graphs in FIG. 1, the number of cells of the primary metal (aluminum) of alloy castings A357-T6 and A356-T6, counted per unit area, 0.0001 psi is plotted against the inverse aspect ratio of the geometric shape of the eutectic (silicon) particles of the alloy. Thus, if a casting zone has a cell count of N=30 and an aspect ratio, AR =1.626 (1/AR =0.615), then the ductility is EL =7.5% for the porosity of P=0.1%. These values are read by reading between the solid graph curves enclosing the circle indicating the location of the cell count and inverse aspect ratio point. These graph lines of 7 and 8% EL designate the circled value to be 7.5% ductility for the porosity value of 0.1%.

Three other values of porosity are indicated by the broken lines, namely 1%, 0.5%, and 0.001%. The EL value for each of the porosity values is that number to the left thereof.

An example of the use of the ductility prediction equation, according to the invention, is as shown in the following table where ductility has been predicted by calculation using the inventive equation for 24 locations of an air launch cruise missile tank 4 casting. Comparison of measured and predicted ductilities are in close agreement as shown in the table. The examined referenced locations are shown in FIGS. 2–5. The black bars are tensile specimens and indicate the locations referred to by reference numerals in the table.

| Location | N | AR | P | EL predicted (%) | EL measured (%) |
|---|---|---|---|---|---|
| 1 | 47.1 | 1.51 | .070 | 12.2 | 10.0 |
| 2 | 47.5 | 1.52 | .147 | 10.7 | 10.7 |
| 3 | 21.8 | 1.58 | .041 | 7.6 | 6.8 |
| 4 | 44.6 | 1.52 | .146 | 10.3 | 4.5 |
| 5 | 43.6 | 1.53 | .209 | 9.3 | 10.0 |
| 6 | 29.8 | 1.60 | .590 | 4.7 | 3.6 |
| 7 | 29.4 | 1.58 | .296 | 6.2 | 6.2 |
| 8 | 30.0 | 1.54 | .191 | 7.5 | 6.4 |
| 9 | 32.6 | 1.63 | .516 | 5.0 | 8.2 |
| 10 | 28.7 | 1.67 | .965 | 3.2 | 3.2 |
| 11 | 33.7 | 1.56 | .172 | 8.0 | 8.7 |
| 12 | 27.4 | 1.55 | .055 | 8.8 | 7.9 |
| 13 | 33.1 | 1.67 | .534 | 4.7 | 4.5 |
| 14 | 30.8 | 1.56 | .178 | 7.5 | 7.9 |
| 15 | 31.8 | 1.60 | .300 | 6.2 | 9.2 |
| 16 | 29.1 | 1.56 | .278 | 6.5 | 5.8 |
| 17 | 30.8 | 1.58 | .140 | 7.6 | 7.6 |
| 18 | 29.4 | 1.57 | .141 | 7.5 | 6.7 |
| 19 | 26.2 | 1.59 | .589 | 4.4 | 6.7 |
| 20 | 28.3 | 1.60 | .198 | 6.5 | 6.6 |
| CC2 | 44.0 | 1.53 | .017 | 13.3 | 12.9 |
| CC3 | 40.8 | 1.54 | .077 | 10.7 | 13.0 |
| CC4 | 45.2 | 1.54 | .116 | 10.7 | 11.1 |
| CC5 | 45.9 | 1.53 | .202 | 9.6 | 10.3 |

In addition to the method of predicting ductility of a metallic cast eutectic alloy, the invention includes the discovery of a microstructural function which accounts for the manufacturing processes that influence ductility, and the microstructural characteristics of the number of cells of a primary metal of the alloy such as aluminum in an aluminum silicon magnesium alloy, the silicon eutectic, and the lack of soundness, i.e., porosity; and the discovery of a ductility prediction equation. This invention applies to any metallic cast eutectic alloy.

The invention and its attendant advantages will be understood from the foregoing description and it will be apparent that various changes may be made in the form, construction, and arrangements of the parts of the invention without departing from the spirit and scope thereof or sacrificing its material advantages, the arrangements hereinbefore described being merely by way of example. I do not wish to be restricted to the specific form shown or uses mentioned except as defined in the accompanying claims.

What is claimed is:

1. A method for nondestructively determining ductility of a casting of a metallic eutectic ally comprising a primary metal and eutectic particles, said method comprising the steps of:

(a) selecting a surface area of said casting for determination of ductility;

(b) determining the number metal cells of said primary metal within said surface area of said casting;

(c) measuring the aspect ratio of the eutectic particles and the porosity within said surface area of said casting;

(d) determining ductility of said casting by relating the number cells of said primary metal per unit area with the measured said aspect ratio of said eutectic particles and the measured said porosity according to the following relationship:

$$EL=10\{[C_1(N^{0.5})-C_2(N^{0.5}/AR)+C_3(-1/AR)-C_4(P^{0.5})-C_5-]/(k+b)\}$$

where

EL is the total average elongation (ductility of said casting in percent;

N is the number of cells of said primary metal of said casting per unit area;

$C_1(N^{0.5})$ is the solidification rate (SR);

$C_2(N^{0.5}/AR)$ is the SR and eutectic modification (EM) interaction; AR is said aspect ratio of said eutectic particles;

$C_3(1/AR)$ is the EM from alloying and solution heat treatment;

$C_4(P^{0.5})$ is the porosity, percent coverage, ductility reduction;

$C_5$ is a coefficient characteristic of the chemistry of said alloy; and c, k, and b are empirical constants for said alloy and $C_1$, $C_2$, $C_3$, and $C_5$ are coefficients from statistical multiple regression of said alloy.

2. The method of claim 1 wherein aluminum is said primary metal and said eutectic particles comprise primarily silicon.

* * * * *